United States Patent
Liu

(10) Patent No.: US 12,324,805 B2
(45) Date of Patent: Jun. 10, 2025

(54) CANCER TREATMENT

(71) Applicant: LDN Pharma Limited, England (GB)

(72) Inventor: Wai Liu, London (GB)

(73) Assignee: LDN Pharma Limited, London (GB)

( * ) Notice: Subject to any disclaimer, the term of this patent is extended or adjusted under 35 U.S.C. 154(b) by 550 days.

(21) Appl. No.: 16/763,821

(22) PCT Filed: Nov. 14, 2018

(86) PCT No.: PCT/EP2018/081244
§ 371 (c)(1),
(2) Date: May 13, 2020

(87) PCT Pub. No.: WO2019/096853
PCT Pub. Date: May 23, 2019

(65) Prior Publication Data
US 2020/0383971 A1 Dec. 10, 2020

(30) Foreign Application Priority Data

Nov. 14, 2017 (EP) ..................................... 17201699

(51) Int. Cl.
*A61K 31/485* (2006.01)
*A61K 31/05* (2006.01)
*A61P 35/00* (2006.01)

(52) U.S. Cl.
CPC ............ *A61K 31/485* (2013.01); *A61K 31/05* (2013.01); *A61P 35/00* (2018.01)

(58) Field of Classification Search
CPC .................................................... A61K 31/485
USPC ....................................................... 514/282
See application file for complete search history.

(56) References Cited

FOREIGN PATENT DOCUMENTS

| JP | 2008-535850 A | 9/2008 |
|---|---|---|
| JP | 2011-500686 A | 1/2011 |
| JP | 2016-210809 A | 12/2016 |
| JP | 2017-519006 A | 7/2017 |
| WO | 2013/057487 A1 | 4/2013 |
| WO | 2015/189597 A1 | 12/2015 |

OTHER PUBLICATIONS

Cridge et al., "Critical appraisal of the potential use of cannabinoids in cancer management," Cancer Management and Research, vol. 5, pp. 301-313, 2013.
McGregor et al., "Rats on the grog: Novel Pharmacotherapies for alcohol craving," Addictive Behavi, vol. 29, No. 7, pp. 1341-1357, 2004.
Allnutt, Sarah, Written Opinion of the International Searching Authority, PCT/EP2018/081244, European Patent Office, Dec. 7, 2018.
Dickson et al., "Development of cell-cycle inhibitors for cancer therapy," Current Oncology, 16(2):38-43, 2009.
Shinkuma, Tadanobu, Office Action, Japan Patent Office, Application No. 2020-526491, Oct. 4, 2022.
Shrivastava, Ashutosh, "Cannabidiol Induces Programmed Cell Death in Breast Cancer Cells by Coordinating the Cross-talk between Apoptosis and Autophagy", Molecular Cancer Therapeutics, Jul. 6, 2011, 10(7):1161-1172.

*Primary Examiner* — Taofiq A Solola
(74) *Attorney, Agent, or Firm* — Gavrilovich, Dodd & Lindsey LLP

(57) ABSTRACT

The present invention is based on the finding that the inhibition of the proliferation of cancer cells by cannabinoids is brought about more effectively by combined treatment with low dose naltrexone (LDN) or 6-β-naltrexone (6BN), a metabolite of naltrexone. There is provided a pharmaceutical composition comprising naltrexone or a metabolite thereof or an analogue thereof, for use in the treatment of cancer within a subject, wherein a therapeutically effective amount of the naltrexone or metabolite thereof or analogue of either is to be administered to the subject in a first treatment phase, wherein after the first treatment phase the subject is to be administered a therapeutically effective amount of a cannabinoid in a second treatment phase.

16 Claims, 2 Drawing Sheets

CANCER TREATMENT

CROSS REFERENCE TO RELATED APPLICATIONS

This application is a U.S. National Stage Application filed under 35 U.S.C. § 371 and claims priority from International Application No. PCT/EP2018/081244, filed Nov. 14, 2018, which application claims the benefit of European Patent Application No. 17201699.0, filed Nov. 14, 2017, the disclosures of which are incorporated herein in their entirety by reference.

FIELD OF THE INVENTION

The invention relates to regimes of drug administration and drug combinations for use in the treatment of cancer.

BACKGROUND TO THE INVENTION

Cannabinoids are a class of phenolic compounds abundantly produced in plants of the *Cannabis* genus. Various cannabinoid compounds have long been known to exhibit psychotropic effects in humans and are widely used recreationally, despite such use being illegal in many jurisdictions.

However, recent research has shown that certain cannabinoids are of therapeutic value against a diverse array of pathologies such as inflammatory disorders, neurodegenerative and psychiatric disorders, chronic pain, anxiety and PTSD. While cannabinoids are currently used to combat the wasting, emesis and nausea associated with cancer treatment, evidence exists which suggests that certain cannabinoid compounds may be effective in treating the underlying pathologies of cancers. Presently available evidence suggests that they do this through disruption of cancer cell migration, adhesion, and tumour vascularisation.

An endogenous cannabinoid-mediated signalling system functions in mammals, and on the balance of evidence probably in most other vertebrates too. In humans, two cannabinoid receptors have been identified and named CB1 and CB2, both of which are part of the G protein-coupled receptor superfamily.

Pharmacological evidence to date suggests that activation of CB1 is responsible for the majority of the psychotropic effects of cannabinoid intake, while therapeutic effects are mostly mediated by CB2. As such, ideal therapeutic molecules will activate CB2 in preference to CB1, alleviating unwanted psychotropic side effects. Cannabidiol (CBD), a component of *Cannabis* extract, is a cannabinoid with this binding profile which has recently generated considerable interest, but whose full mechanism of action is still being elucidated.

In general however, natural cannabinoids do not tend to show high specificity for one or other receptor, but newly developed synthetic cannabinoids are available which bind more specifically, for example JWH-133 and SR141716 (Cridge & Rosengren 2013). These compounds have been shown to inhibit tumour growth and cancer cell viability both in vitro and in various tumour-implanted mouse models.

It is sometimes the case that receptors in one signalling pathway, responsive to a particular ligand, can have their expression levels or downstream effects altered by a change in the signalling output of another seemingly separate signalling pathway. Such cross-modulation has been demonstrated between, for example, the signalling pathways following activation of the Growth Hormone and insulin receptors.

SUMMARY OF THE INVENTION

It has been found by the present inventors that the inhibition of the proliferation of cancer cells by cannabinoids is brought about more effectively by combined treatment with low dose naltrexone (LDN) or 6-β-naltrexol (6BN), a metabolite of naltrexone. They also found that the effectiveness of such treatment is surprisingly dependent on the order in which the two agents are administered, with the most effective regime being a phase of treatment with LDN or 6BN followed by a phase of treatment with a cannabinoid.

The inventors have also made the previously unknown finding that treatment with LDN or 6BN brings about a significant increase in levels of the CB2 receptor in cancer cells, thus allowing the cannabinoid to be more effective.

According to a first aspect of the invention, there is provided a pharmaceutical composition comprising naltrexone or a metabolite thereof or an analogue selected from the group consisting of methylnaltrexone, naloxone, nalmefene and nalorphine, for use in the treatment of cancer within a subject, wherein a therapeutically effective amount of the naltrexone or metabolite thereof or analogue is to be administered to the subject in a first treatment phase, wherein after the first treatment phase the subject is to be administered a therapeutically effective amount of a cannabinoid in a second treatment phase.

According to a second aspect of the invention, there is provided a pharmaceutical composition comprising a cannabinoid for use in the treatment of cancer within a subject, wherein said subject is characterised in having undergone a first treatment phase during which the subject is administered a therapeutically effective amount of naltrexone or a metabolite thereof or an analogue selected from the group consisting of methylnaltrexone, naloxone, nalmefene and nalorphine, and wherein following the first treatment phase a therapeutically effective amount of said cannabinoid is to be administered to the subject.

According to a third aspect of the invention, there is provided a preparation comprising naltrexone or a metabolite thereof or an analogue selected from the group consisting of methylnaltrexone, naloxone, nalmefene and nalorphine, and a cannabinoid for use in the treatment of cancer within a subject, wherein the naltrexone or metabolite thereof or analogue is provided in a therapeutically effective amount to be administered in a first treatment phase, wherein the cannabinoid is provided in a therapeutically effective amount to be administered in a second treatment phase following the first treatment phase.

According to a fourth aspect of the invention, there is provided a method for determining the suitability of a subject with cancer for treatment with a cannabinoid in a second treatment phase, said subject characterised in having undergone a first treatment phase as defined above, the method comprising the steps of:

i. contacting a sample obtained from the subject after or during a recovery phase with a probe specific for CB2;
ii. determining the concentration of CB2 within the sample; and
iii. comparing the concentration of CB2 within the sample with a concentration of CB2 determined from a sample obtained from the subject before the first treatment phase, wherein if the CB2 concentration has increased by at least two-fold after the first treatment phase, the subject is suitable for the second treatment phase.

According to a fifth aspect of the invention, there is provided the use of naltrexone or a metabolite thereof or an analogue selected from the group consisting of methylnaltrexone, naloxone, nalmefene and nalorphine, in the manufacture of a medicament for the treatment of cancer within a subject, wherein the medicament is to be administered to a subject in a first treatment phase of a combined treatment regimen, said treatment regimen comprising the first treatment phase followed by a second treatment phase, wherein the subject is to be administered a cannabinoid in the second treatment phase.

According to a sixth aspect of the invention, there is provided the use of a cannabinoid in the manufacture of a medicament for the treatment of cancer in a subject, wherein said medicament is to be administered in a second treatment phase of a combined treatment regimen, said treatment regimen comprising a first treatment phase followed by the second treatment phase, wherein the subject is to be administered naltrexone or a metabolite thereof or an analogue selected from the group consisting of methylnaltrexone, naloxone, nalmefene and nalorphine, in the first treatment phase.

According to a seventh aspect of the invention, there is provided the use of naltrexone or a metabolite thereof or an analogue selected from the group consisting of methylnaltrexone, naloxone, nalmefene and nalorphine, in the manufacture of a first medicament and the use of a cannabinoid in the manufacture of a second medicament, both medicaments for the treatment of cancer, wherein the first and second medicaments are to be administered to a subject with cancer in a combined treatment regimen, said treatment regimen comprising a first treatment phase followed by a second treatment phase, wherein the first medicament is to be administered to the subject during the first treatment phase and the second medicament is to be administered to the subject in the second treatment phase.

According to an eighth aspect of the invention there is provided a method for the treatment of cancer in a subject comprising administering to the subject in a first treatment phase a therapeutically effective amount of naltrexone or a metabolite thereof or an analogue selected from the group consisting of methylnaltrexone, naloxone, nalmefene and nalorphine, followed by administering to the subject in a second treatment phase a therapeutically effective amount of a cannabinoid.

DETAILED DESCRIPTION OF THE INVENTION

Figure 1:
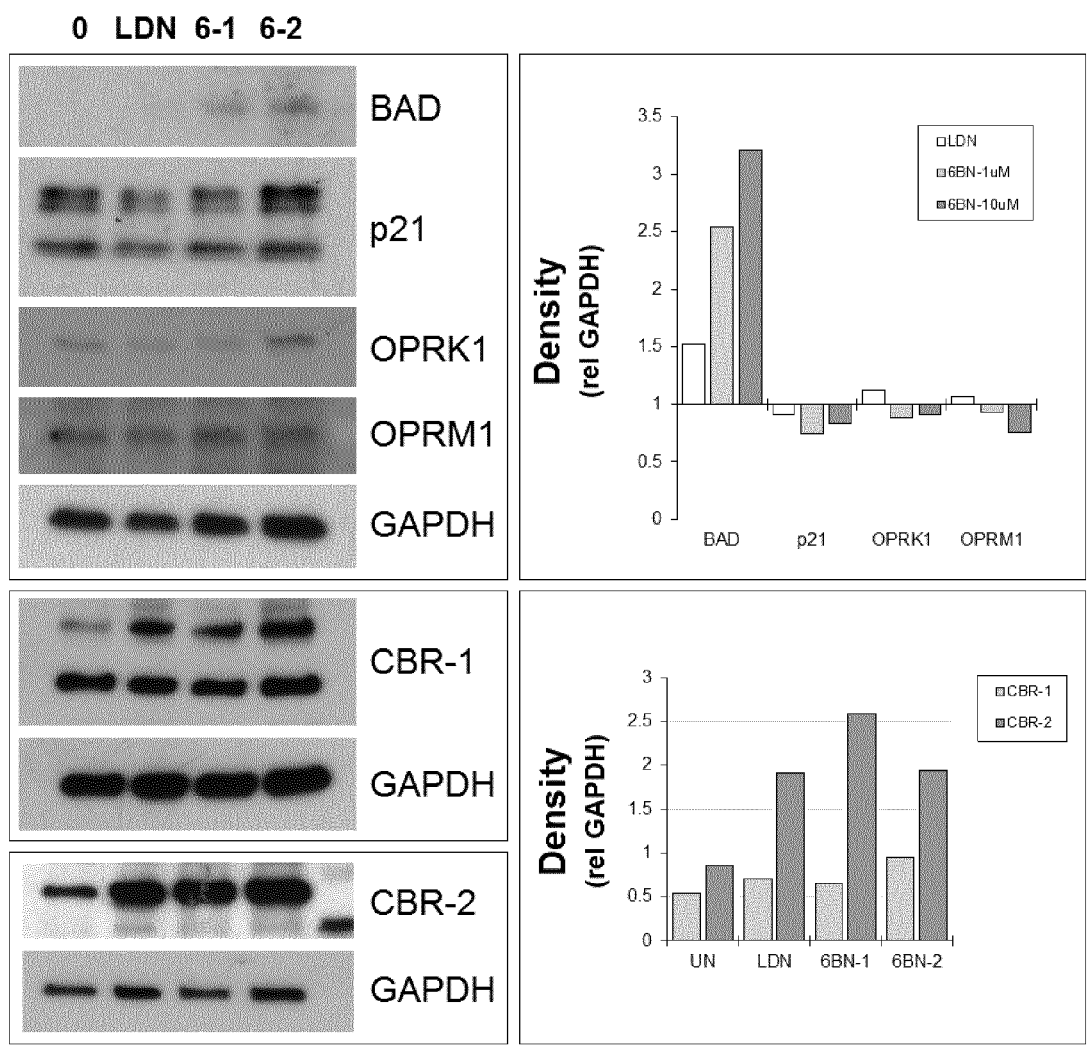
FIG. 1 shows the effects of treatment for two days with naltrexone at 10 nM (LDN), 6-β-naltrexol at 1 µM (6-1), or 6-β-naltrexol at 10 µM (6-2) on cultures of the MCF7 breast cancer cell line. Levels of Bcl2-associated death promoter (BAD), p21 protein, the opioid receptors kappa 1 (OPRK1) and mu 1 (OPRM1), and the cannabinoid receptors CBR1 (CB1) and CBR2 (CB2) are visualised by Western blot (left) against GAPDH as a loading control, and quantified via density analysis relative to GAPDH (right).

The invention provides a specific therapeutic regimen for treating cancer in a subject, wherein a cannabinoid is administered after administration of Low Dose Naltrexone (LDN), a metabolite of naltrexone, or an analogue thereof selected from the group consisting of methylnaltrexone, naloxone, nalmefene and nalorphine.

The phased administration of LDN and then a cannabinoid has been found by the inventors to inhibit cancer cell proliferation more effectively than separate or simultaneous administration, or phased administration of a cannabinoid and then LDN.

It was also found that levels of the CB2 receptor increased significantly in MCF7 cells after treatment with LDN. Without wishing to be bound by theory, this increase in CB2, which is the therapeutic target of cannabinoids such as CBD, is feasibly a contributing factor to the increase in the effectiveness of the treatment with CBD.

The skilled person will be able to carry out the phased administration of the therapeutic agents as described. The invention can be further understood with reference to the following definitions:

As used herein, "naltrexone" refers to the compound 17-cyclopropylmethyl-4.5α-epoxy-3,14-dihydroxymorphinan-6-one (with IUPAC name (4R,4aS,7aR,12bS)-3-(cyclopropylmethyl)-4a,9-dihydroxy-2,4,5,6,7a,13-hexahydro-1H-4,12-methanobenzofuro[3,2-e]isoquinoline-7-one) and pharmaceutically acceptable salts, solvates, hydrates, racemates, stereoisomers, clathrates, polymorphs and prodrugs thereof. Analogues thereof are also envisaged for use as per the invention. Suitable analogues include methylnaltrexone, naloxone, nalmefene and nalorphine.

The naltrexone is typically in its hydrochloride salt form.

"Low Dose Naltrexone" (LDN) refers to naltrexone administered in "low" doses of less than 0.5 mg/kg, preferably less than 0.2 mg/kg, more preferably between 0.01 mg/kg and 0.08 mg/kg, even more preferably between 0.03 mg/kg and 0.06 mg/kg, most preferably between 0.04 mg/kg and 0.05 mg/kg. Typically, a low dose is up to 3 mg per day in total, per patient.

Metabolites of naltrexone include 6-β-naltrexol, 2-hydroxy-3-methoxy-6β-naltrexol and 2-hydroxy-3 methoxynaltrexone.

The preferred metabolite of naltrexone is 6-β-naltrexol (6BN), which as used herein refers to the compound N-cyclopropylmethyl-7,8-dihydro-14-hydroxynorisomorphine (with IUPAC name (4R,4aS,7R,7aR,12bS)-3-(cyclopropylmethyl)-1,2,4,5,6,7,7a,13-octahydro-4,12-methanobenzofuro[3,2-e]isoquinoline-4a,7,9-triol), and pharmaceutically acceptable salts, solvates, hydrates racemates, stereoisomers, clathrates, polymorphs, and prodrugs thereof.

The 6BN or analogues etc, may also be administered at "low dose". In this context, a "low dose" can be the same as that outlined above for naltrexone.

Cannabinoids are a class of compounds understood by the skilled person which comprise those abundantly made by plants of the *Cannabis* genus, as well as endocannabinoids which are synthesised in animals. Synthetic compounds active against CB receptors are also envisaged. When used herein the term can refer to any cannabinoid, but is preferably selected from the list containing cannabidiol, cannabidiolic acid, cannabinol, cannabigerol, cannabivarin, tetrahydrocannabivarin, cannabidivarin, cannabichromene, arachidonoylethanolamine, 2-arachidonoylglycerol, 2-arachidonoyl glyceryl ether, N-arachidonoyl dopamine, virodhamine, dronabinol, nabilone, rimonabant, R-(+)-Met-anandamide, WIN-55,212-2, HU-210, JWH-133, SR141716, SR144528 or combinations thereof, or pharmaceutically acceptable salts, solvates, hydrates, racemates, stereoisomers, clathrates, polymorphs, prodrugs, and analogues thereof which bring about equivalent effects.

In certain embodiments, where the agent is 6-β-naltrexol, 6-β-naltrexol is to be administered in an amount effective to increase the blood plasma concentration of 6-β-naltrexol to at least 0.34 ng/ml, preferably at least 3.4 ng/ml, more preferably at least 34 ng/ml, or most preferably at least 340 ng/ml. In certain embodiments, 6-β-naltrexol is to be administered in an amount effective to increase the blood plasma concentration of 6-β-naltrexol to within the range of 0.3 ng/ml to 3,400 ng/ml, preferably to within the range of from 34 ng/ml to 3,400 ng/ml, more preferably within the range of 340 ng/ml to 3,400 ng/ml. The amount effective to achieve such an amount can be determined using any number of conventional techniques known to the person skilled in the art. For example, the skilled person could perform mass spectrometry on a blood plasma sample obtained from the subject in order to determine the increase in the concentration of 6-β-naltrexol within the sample after administration of an amount of 6-β-naltrexol. The effective amount is the amount determined to bring about the desired increase in blood plasma concentration. Typically, the naltrexol will be administered in an amount up to 3 mg per day per patient.

The cannabinoid can be administered at conventional amounts based on the particular cannabinoid and the details of the patient. In certain embodiments, the cannabinoid is to be administered each day in doses of between 10 mg and 1000 mg, preferably between 200 and 800 mg, more preferably between 300 and 500 mg.

As used herein, a "preparation" can refer to a substance or a collection of substances, in the form of one or more compositions intended for use either simultaneously or non-simultaneously.

The method of administration is not particularly limited for either therapeutic agent, but in various embodiments of the invention, LDN and cannabinoids are administered via the oral, buccal, sublingual, nasal, pulmonary, intravenous, rectal, topical, and transdermal routes. For LDN administration is preferably oral, and for cannabinoids it is preferably sublingual.

The treatment regimen envisaged comprises a "first treatment phase" and a "second treatment phase". In the first treatment phase, a therapeutically effective amount of LDN, a metabolite thereof, or an analogue of either is administered. In the second treatment phase, an effective amount of one or more cannabinoids is administered.

It is preferred that the second treatment phase begins only after 1 to 7 days have elapsed from the start of the first treatment phase, more preferably 1 to 4 days, most preferably 1 to 2 days, a "day" being a continuous period of 24 hours.

In a further preferred embodiment of the invention, there is a "recovery phase" in between the end of the first treatment phase and the start of the second treatment phase. During the recovery phase no LDN or cannabinoid is administered. In one embodiment the recovery phase has a duration of at least two days, preferably no more than 1 week apart, most preferably the duration is two days.

As used herein, the terms "treating" and "treatment" and "to treat" refer to both therapeutic measures that cure, slow down, and/or halt progression of a diagnosed pathologic condition or disorder, and also to prophylactic or preventative measures that prevent and/or slow the development of a targeted pathologic condition or disorder. Therefore, those in need of treatment include those already with the disorder, those prone to have the disorder, and those in whom the disorder is to be prevented. In some instances, a subject is successfully "treated" for a tumour/cancer according to the present invention if the subject shows one or more of the following: a reduction in the number of, or complete absence of, cancer cells; a reduction in the tumour size; inhibition of, or an absence of, cancer cell infiltration into peripheral organs including, for example, the spread of cancer into soft tissue and bone; inhibition of, or an absence of, tumour metastasis; inhibition of, or an absence of, tumour growth; reduced morbidity and mortality; reduction in tumourigenicity, tumourigenic frequency, or tumourigenic capacity of a tumour; reduction in the number or frequency of cancer stem cells in a tumour; differentiation of tumourigenic cells to a non-tumourigenic state; or some combination of effects.

As used herein, the term "subject" refers to any animal, including but not limited to humans, non-human primates, horses, canines, felines, rodents, and other vertebrates which are to be the recipient of a treatment for cancer. The terms "subject" and "patient" are used interchangeably herein.

As used herein, the term "tumour/cancer" refers to any mass of tissue that results from excessive cell growth, proliferation and/or survival, either benign (noncancerous) or malignant (cancerous), including pre-cancerous lesions.

The types of cancer treatable by the invention are not in any way limited, and include, for example, carcinoma, sarcoma, adenocarcinoma, melanoma, neural (blastoma, glioma), mesothelioma and reticuloendothelial, lymphatic or haematopoietic neoplastic disorders (e.g., myeloma, lymphoma or leukemia). In particular embodiments, the tumour can include a lung adenocarcinoma, lung carcinoma, diffuse or interstitial gastric carcinoma, colon adenocarcinoma, prostate adenocarcinoma, oesophagus carcinoma, breast carcinoma, pancreas adenocarcinoma, ovarian adenocarcinoma, adenocarcinoma of the adrenal gland, adenocarcinoma of the endometrium or uterine adenocarcinoma, but the type of cancer is preferably breast cancer.

In a preferred embodiment the cancer to be treated is selected from brain, breast, colon, lung, prostate and pancreatic cancer, and leukaemia. The cancer to be treated is preferably breast cancer.

The definition of "breast cancer" is well known in the medical sciences. The skilled person will appreciate that breast cancer refers to any malignancy of the breast tissue of men or women, including, for example, carcinomas and sarcomas. Particular embodiments of breast cancer include ductal carcinoma in situ (DCIS), lobular carcinoma in situ (LCIS), or mucinous carcinoma. Breast cancer also refers to infiltrating ductal (IDC), lobular neoplasia or infiltrating lobular carcinoma (ILC).

As used herein, the term "cancer cell" refers to a cell or immortalized cell line derived from tumour or cancer.

In one aspect of the invention is provided a method for determining the suitability of a subject, who has cancer and has already been treated with LDN, for treatment with a cannabinoid. In this aspect, a sample is to be obtained from the subject and contacted with a CB2-specific probe. The concentration of CB2 in the sample is thereby determined and compared with a reference measurement made before the first treatment phase.

As used herein, "suitability" refers to the property of having a high probability of treatment, as defined above, being successful, compared to those subjects deemed unsuitable by the test. A subset of subjects undergoing testing by the method envisaged in one aspect of this invention will be deemed to be unsuitable for the second phase of treatment. In no way is any part of the invention disallowed for use on such subjects. The method of determining suitability is intended to be considered by the skilled person alongside other tests known to them and exercising their intuition and judgement.

In certain embodiments, the biological "sample" obtained from the subject for use in the method is blood, plasma, serum, lymph fluid, a tissue, or cells derived from a tissue sample. Preferably however, the sample is a tumour biopsy obtained from the subject.

As used herein, the "probe" is any moiety which, on contacting the sample obtained from the subject, allows in some way the measurement of the concentration of CB2 in the sample. In one embodiment, this probe is an antibody or other CB2-binding molecule used in the provision of a purer solution of CB2 which can be analysed spectrophotometrically and through calibration using methods known to the skilled person, the concentration of CB2 in the original sample can be determined.

In another aspect is provided the use of naltrexone, metabolites thereof, or analogue selected from the group consisting of methylnaltrexone, naloxone, nalmefene and nalorphine, and cannabinoids in the manufacture of a medicament to be administered as part of a "combined treatment regimen", which as used herein refers to the regimen consisting of the first treatment phase, preferable recovery phase, and second treatment phase, as defined above.

The invention will now be described with reference to the following non-limiting examples.

EXAMPLES

Example 1

One illustrative and non-limiting experiment was carried out on cultures of MCF7 cells. In brief, either LDN at 10 nM or 6BN at 1 µM or 10 µM was administered in vitro to a culture for two days, after which the expression levels of BAD, p21, opioid receptors kappa and mu, CB1, CB2, and GAPDH (as a loading control) were analysed via Western blot and subsequent quantification via density measurement of the bands.

In full, MCF7 cells were seeded into 6-well plates at a density of $1 \times 10^5$/well and left to adhere over-night. Naltrexone (10 nM) or 6-β-naltrexol (1 µM or 10 µM) were added to the cells before harvesting cells for western blot analysis. Primary probing was performed with specific antibodies generated against BAD, p21, OPRK1, OPRK2, CBR-1 and CBR-2. BAD is Blc2-associate death promoter, a pro-apoptotic protein which, if upregulated in cancer cells, increases their tendency to be killed by a variety of therapies. Anti-GAPDH was used as a loading control. All antibodies were used at a dilution of 1:1000, followed by the appropriate HRP conjugated secondary antibodies also at a dilution of 1:1000. Bands were visualised by the SuperSignal chemiluminescent detection system, and densitometry of band intensity was determined using Adobe Photoshop CS3, v10.0, and normalised to the loading control.

In response to all three treatments, levels of CB2 and BAD rose relative to the controls in which no drug was administered. For CB2, the rise was highest in response to administration of 10 µM 6BN. This can be seen in FIG. 1.

Example 2

Another illustrative and non-limiting experiment was carried out on cultures of MCF7 cells. In brief, the cultures were treated with LDN or 6BN for two days, after which a cannabinoid was administered for a further two days. Cell number and viability were assessed on day four. The sequence of the administration for each therapeutic agent was reversed and the experiment repeated.

In full, MCF7 cells were seeded into 6-well plates at a density of $1.5 \times 10^4$/well and left to adhere. Cells were then cultured with naltrexone (10 nM), 6-β-naltrexol (10 µM) or cannabidiol (10 µM). Drug-containing media was removed after 48 h, and cells were rinsed gently with drug-free medium. Fresh culture medium was then added to the cells supplemented with either naltrexone (10 nM), 6-β-naltrexol (10 µM) or cannabidiol (10 µM), as indicated in the graph. Cell number and viability were assessed a further 48 h later, with percentages of live and dead cells being discriminated by trypan blue dye exclusion. Data were then consolidated to compare the effect of sequence on overall effect.

Figure 2:
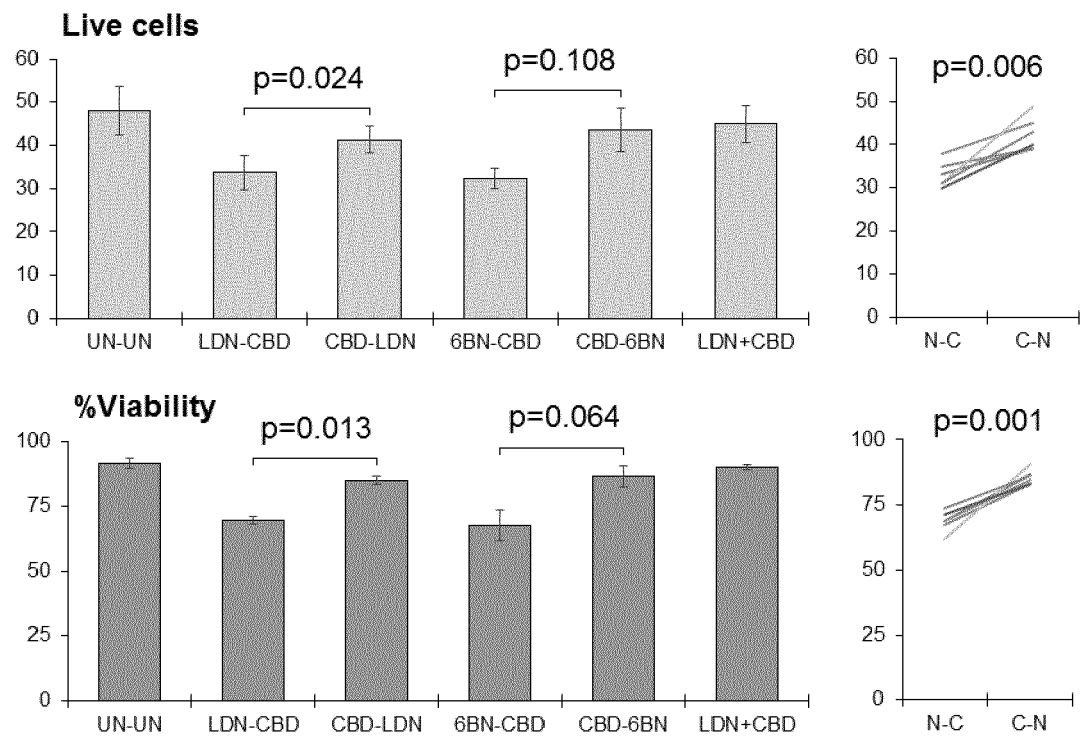
FIG. 2 shows the effect of various two-stage treatments on the proliferation and viability of MCF7 cells. Each treatment lasted four days and consisted of two days of treatment with the first agent (UN=control, LDN=Low Dose Naltrexone at 10 nM CBD=Cannabidiol, 6BN=6-β-naltrexol) before the second-named agent was introduced for a further two days.

As can be seen in FIG. 2, it was found that schedules in which LDN or 6BN were utilised before the cannabinoid had a greater effect on inhibiting the proliferation of the cancer.

REFERENCES

Cridge, B. & Rosengren, R (2013) Critical appraisal of the potential use of cannabinoids in cancer management. *Cancer Management and Research* 2013:5 301-313

The invention claimed is:

1. A method of treating cancer within a subject comprising administering to the subject a pharmaceutical composition comprising:
   naltrexone; or
   6-β-naltrexol, 2-hydroxy-3-methoxy-6β-naltrexol or 2-hydroxy-3 methoxy-naltrexone; or
   an analogue selected from the group consisting of methylnaltrexone, naloxone, nalmefene and nalorphine;
   wherein the pharmaceutical composition is administered in a therapeutically effective amount in a first treatment phase, wherein after the first treatment phase the subject is to be administered a therapeutically effective amount of a cannabinoid in a second treatment phase.

2. A method of treating cancer within a subject, wherein said subject is characterized in having undergone a first treatment phase during which the subject is administered a preparation comprising a therapeutically effective amount of:
   naltrexone; or
   6-β-naltrexol, 2-hydroxy-3-methoxy-6β-naltrexol or 2-hydroxy-3 methoxy-naltrexone; or
   an analogue selected from the group consisting of methylnaltrexone, naloxone, nalmefene and nalorphine,
   and wherein following the first treatment phase a therapeutically amount of a cannabinoid is to be administered to the subject in a second treatment phase.

3. A method of treating cancer within a subject comprising administering to the subject a preparation comprising:
   naltrexone; or
   6-β-naltrexol, 2-hydroxy-3-methoxy-6β-naltrexol or 2-hydroxy-3 methoxy-naltrexone; or an analogue selected from the group consisting of methylnaltrexone, naloxone, nalmefene and nalorphine, and a cannabinoid,
wherein the naltrexone or 6-β-naltrexol, 2-hydroxy-3-methoxy-6β-naltrexol or 2-hydroxy-3 methoxy-naltrexone or analogue of either is provided in a therapeutically effective amount to be administered in a first treatment phase, wherein the cannabinoid is provided in a therapeutically effective amount to be administered in a second treatment phase following the first treatment phase.

4. The method according to claim 1, 2 or 3, wherein the first treatment phase comprises administration for at least two days.

5. The method according to claim 1, 2 or 3, wherein the first treatment phase and second treatment phase are separated by a recovery phase, said recovery phase characterised by the absence of administration of either the naltrexone or metabolite or analogue and the cannabinoid.

6. The method according to claim 5, wherein the recovery phase is for at least one day to 7 days.

7. The method according to claim 1, 2 or 3, wherein the second treatment phase comprises administration for at least one day.

8. The method according to claim 1, 2 or 3, wherein the composition or preparation comprises naltrexone.

9. The method according to claim 1, 2 or 3, wherein the composition or preparation comprises 6-β-naltrexol.

10. The method according to claim 1, 2 or 3, wherein the cannabinoid is selected from the group consisting of cannabidiol, cannabidiolic acid, cannabinol, cannabigerol, cannabivarin, tetrahydrocannabivarin, cannabidivarin, cannabichromene, arachidonoylethanolamine, 2-arachidonoylglycerol, 2-arachidonoyl glyceryl ether, N-arachidonoyl dopamine, virodhamine, dronabinol, nabilone, rimonabant and any combinations thereof.

11. The method according to claim 1, 2 or 3, wherein the cannabinoid is cannabidiol.

12. The method according to claim 1, 2 or 3, wherein the cancer is breast cancer.

13. A method for determining the suitability of a subject with cancer for treatment with a cannabinoid in a second treatment phase, said subject having undergone a first treatment phase with a composition or preparation comprising:
    naltrexone; or
    6-β-naltrexol, 2-hydroxy-3-methoxy-6β-naltrexol or 2-hydroxy-3 methoxy-naltrexone; or
    an analogue selected from the group consisting of methylnaltrexone, naloxone, nalmefene and nalorphine,
    the method comprising the steps of:
        i. contacting a sample obtained from the subject after or during a recovery phase with a probe specific for CB2;
        ii. determining the concentration of CB2 within the sample; and
        iii. comparing the concentration of CB2 within the sample with a concentration of CB2 determined from a sample obtained from the subject before the first treatment phase,
    wherein if the CB2 concentration has increased by at least two-fold after first treatment phase, the subject is suitable for the second treatment phase.

14. The method of claim 13, wherein the sample is a tumour biopsy obtained from the subject.

15. The method according to claim 13, wherein the subject has breast cancer.

16. The method of claim 1, wherein the pharmaceutical composition is administered at a dose of less than 0.5 mg/kg and the cannabinoid is administered at less than 1000 mg/day.

* * * * *